(12) United States Patent
Maki et al.

(10) Patent No.: US 12,653,556 B2
(45) Date of Patent: Jun. 16, 2026

(54) ASPIRATION DEVICE, ASPIRATION SYSTEM, AND ASPIRATION METHOD

(71) Applicant: TERUMO KABUSHIKI KAISHA, Tokyo (JP)

(72) Inventors: Shin Maki, Ebina Kanagawa (JP); Masashi Usami, Tokyo (JP); Shinichi Kaneda, Odawara Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 299 days.

(21) Appl. No.: 18/472,096

(22) Filed: Sep. 21, 2023

(65) Prior Publication Data

US 2024/0008885 A1    Jan. 11, 2024

Related U.S. Application Data

(63) Continuation of application No. PCT/JP2022/002041, filed on Jan. 20, 2022.

(30) Foreign Application Priority Data

Mar. 23, 2021    (JP) ................................. 2021-049219

(51) Int. Cl.
*A61B 17/22*        (2006.01)

(52) U.S. Cl.
CPC .... *A61B 17/22* (2013.01); *A61B 2017/22079* (2013.01)

(58) Field of Classification Search
CPC .......... A61B 17/22; A61B 2017/22079; A61B 2017/00154; A61B 2017/00172;
(Continued)

(56) References Cited

U.S. PATENT DOCUMENTS

| | | | |
|---|---|---|---|
| 8,690,907 B1 * | 4/2014 | Janardhan | ............ A61B 17/221 606/200 |
| 10,183,145 B2 * | 1/2019 | Yang | .................. A61B 17/2202 |

(Continued)

FOREIGN PATENT DOCUMENTS

| | | |
|---|---|---|
| JP | 2005-110790 A | 4/2005 |
| JP | 2019-511943 A | 5/2019 |
| JP | 2020-526293 A | 8/2020 |

OTHER PUBLICATIONS

English Translation of International Search Report dated Apr. 5, 2022 mailed in counterpart International Application No. PCT/JP2022/002041, 2 pages.

(Continued)

*Primary Examiner* — Rebecca E Eisenberg
*Assistant Examiner* — Brandon W. Levy
(74) *Attorney, Agent, or Firm* — Kim & Stewart LLP

(57)        ABSTRACT

An aspiration device for aspirating an object in a blood vessel, includes a pump connectable to an aspiration catheter and capable of applying a negative pressure to the aspiration catheter, and a controller configured to: acquire a length of an abnormal part of the blood vessel in which the object exists and an occlusion rate of the abnormal part, select either a first aspiration mode in which the pressure applied to the aspiration catheter is maintained at a certain level or a second aspiration mode in which the pressure is varied, and control the pump to apply the pressure according to the selected aspiration mode.

18 Claims, 7 Drawing Sheets

(58) Field of Classification Search
CPC .... A61B 2017/22067; A61B 2217/005; A61B 17/12109; A61B 2017/22002; A61B 2018/0041; A61M 1/00; A61M 1/84; A61M 25/10; A61M 2025/0042; A61M 2210/12; A61M 2202/06; A61M 1/3613; A61F 2002/016; A61F 2/011
See application file for complete search history.

(56) References Cited

U.S. PATENT DOCUMENTS

| | | | |
|---|---|---|---|
| 10,478,211 B2 | 11/2019 | Stulen et al. | |
| 2006/0078448 A1* | 4/2006 | Holden | F04B 43/1253 |
| | | | 417/477.2 |
| 2011/0118660 A1* | 5/2011 | Torrance | A61B 17/320758 |
| | | | 604/35 |

OTHER PUBLICATIONS

English Translation of Written Opinion dated Apr. 5, 2022, mailed in counterpart International Application No. PCT/JP2022/002041, 3 pages.

\* cited by examiner

| | LENGTH OF LESION (THRESHOLD 7 mm) | FLOW PASSAGE OCCLUSION RATE OF LESION (THRESHOLD 50%) | ASPIRATION MODE | CONTROL OF ASPIRATION FLOW RATE IN SECOND ASPIRATION MODE |
|---|---|---|---|---|
| THIRD QUADRANT | 3 mm | 30 % | FIRST ASPIRATION MODE | |
| FOURTH QUADRANT | 5 mm | 85 % | SECOND ASPIRATION MODE | LOW FLOW RATE MODE |
| SECOND QUADRANT | 15 mm | 30 % | SECOND ASPIRATION MODE | HIGH FLOW RATE MODE |
| FIRST QUADRANT | 20 mm | 70 % | SECOND ASPIRATION MODE | HIGH FLOW RATE MODE (or ANOTHER MODE IN WHICH ASPIRATION FLOW RATE IS FURTHER HIGH) |

ASPIRATION DEVICE, ASPIRATION SYSTEM, AND ASPIRATION METHOD

CROSS-REFERENCE TO RELATED APPLICATION

This application is a continuation of International Patent Application No. PCT/JP2022/002041 filed Jan. 20, 2022, which is based upon and claims the benefit of priority from Japanese Patent Application No. 2021-049219, filed on Mar. 23, 2021, the entire contents of which are incorporated herein by reference.

FIELD

Embodiments described herein relate generally to an aspiration device, an aspiration system, and an aspiration method.

BACKGROUND

As one of treatment methods for removing a foreign substance such as thrombus in a blood vessel, there is known a method for inserting an aspiration catheter having an aspiration passage formed therein into the blood vessel, and aspirating the foreign substance from an aspiration port to the aspiration passage to remove the foreign substance to the outside of a living body through the aspiration passage.

However, such a foreign substance at a lesion in the blood vessel may or may not be easily aspirated through the aspiration catheter according to a state of the lesion or the like.

SUMMARY OF THE INVENTION

Embodiments of the present disclosure is to provide an aspiration device and an aspiration system capable of performing aspiration control for removing a foreign substance according to a state of a lesion in a blood vessel.

According to an aspect of the present disclosure, an aspiration device for aspirating an object in a blood vessel, comprises a pump connectable to an aspiration catheter and capable of applying a negative pressure to the aspiration catheter; and a controller configured to: acquire a length of an abnormal part of the blood vessel in which the object exists and an occlusion rate of the abnormal part, select either a first aspiration mode in which the pressure applied to the aspiration catheter is maintained at a certain level or a second aspiration mode in which the pressure is varied, and control the pump to apply the pressure according to the selected aspiration mode.

The above-described aspiration device is capable of performing aspiration control for removing a foreign object in a blood vessel according to the state of a lesion in the blood vessel.

BRIEF DESCRIPTION OF THE DRAWINGS

FIG. 1 is a diagram illustrating an aspiration system according to an embodiment.

FIG. 5 is a diagram illustrating an example of aspiration control by the aspiration device according to the states of the specified lesion.

DETAILED DESCRIPTION

Figure 2A:
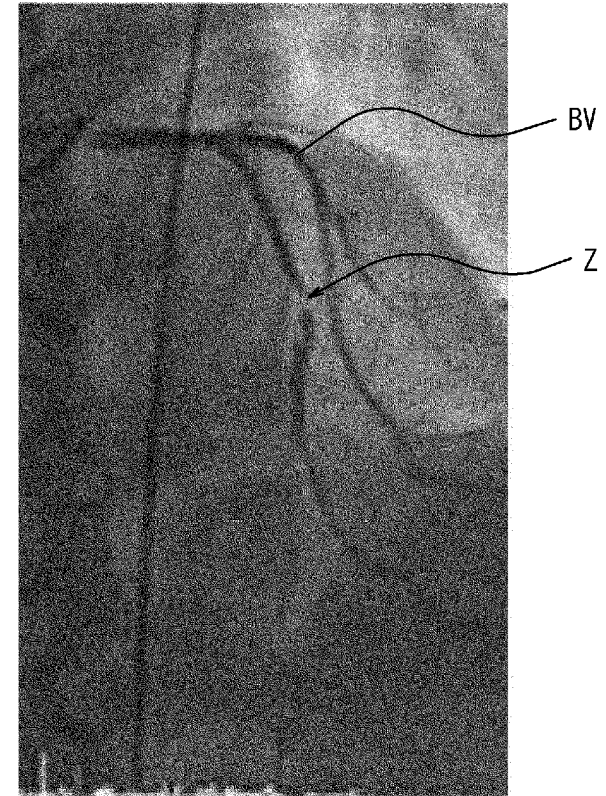
FIG. 2A is a view illustrating an example of an X-ray image acquired by an X-ray image processing device.

Hereinafter, embodiments of an aspiration device and an aspiration system according to the present disclosure will be described with reference to the drawings. In the drawings, the same components are denoted by the same reference numerals.

Figure 1:
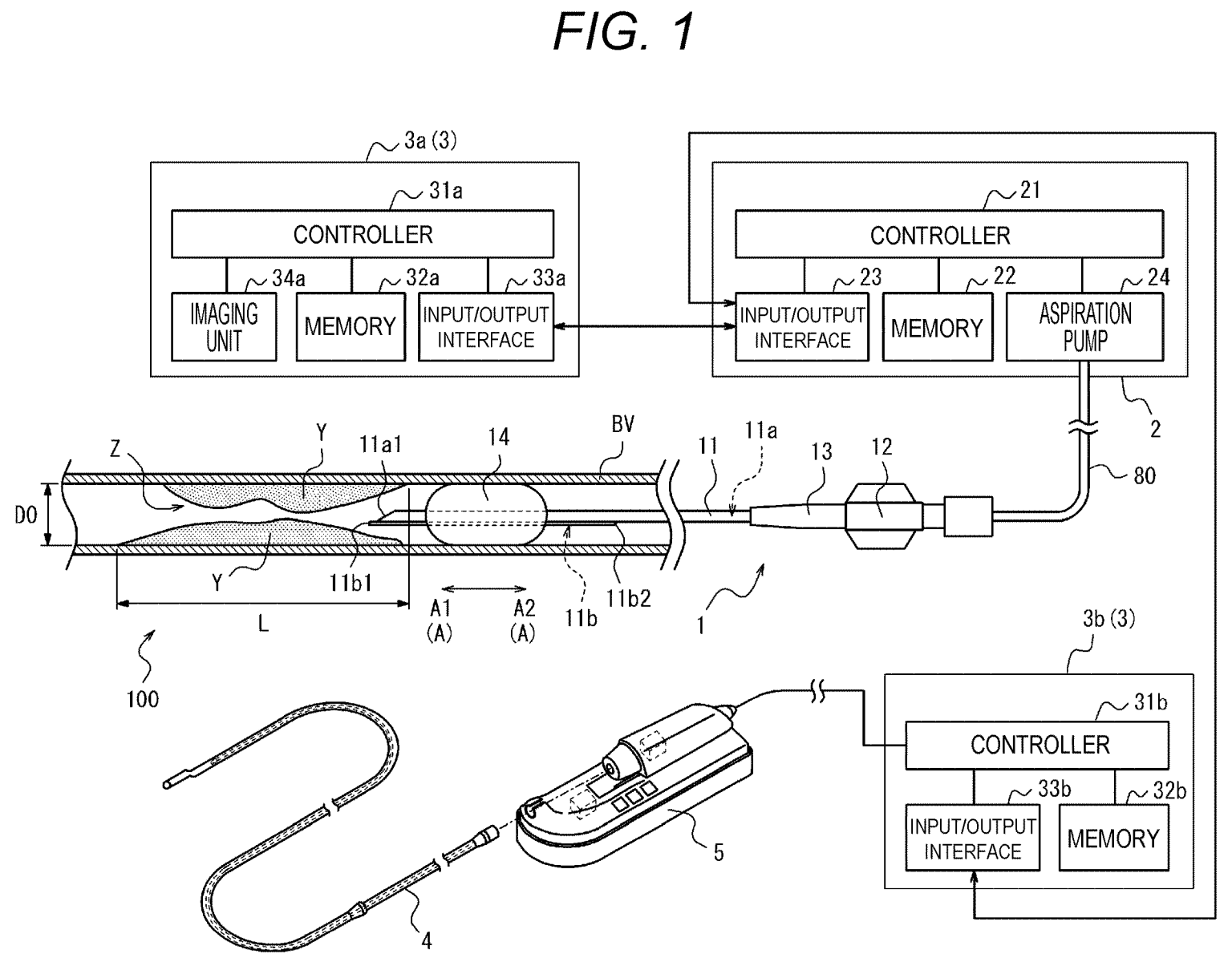

FIG. 1 is a diagram illustrating an aspiration system 100 according to an embodiment of the present disclosure. As illustrated in FIG. 1, the aspiration system 100 of the present embodiment includes an aspiration catheter 1, an aspiration device 2, and an imaging device 3. The imaging device 3 includes an X-ray image processing device 3a and an ultrasound image processing device 3b.

As illustrated in FIG. 1, the aspiration catheter 1 can be inserted into a blood vessel By. The aspiration catheter 1 of the present embodiment includes a tubular catheter body 11, a hub 12, a covering tube 13, and a balloon 14.

The catheter body 11 is a portion (hereinafter, simply referred to as an "insertion portion") that can be inserted into a living body. On the other hand, the hub 12 and the covering tube 13 are portions that are not inserted into the living body (hereinafter, simply referred to as a "non-insertion portion"). The hub 12 and the covering tube 13 are positioned outside the living body in a state in which the catheter body 11 is inserted into the living body, and are operated by an operator. Hereinafter, for convenience of description, in a longitudinal direction A of the catheter body 11, which is the longitudinal direction of the aspiration catheter 1, a direction from the non-insertion portion toward the insertion portion is referred to as a "distal" direction A1. Furthermore, in the longitudinal direction A of the catheter body 11, a direction from the insertion portion toward the non-insertion portion is referred to as a "proximal" direction A2.

As illustrated in FIG. 1, the tubular catheter body 11 has an aspiration flow passage 11a and a guide wire insertion hole 11b. The diameter of the guide wire insertion hole 11b of the present embodiment is smaller than the diameter of the aspiration flow passage 11a. The guide wire insertion hole 11b extends in the longitudinal direction A along the aspiration flow passage 11a. In other words, the aspiration flow passage 11a and the guide wire insertion hole 11b do not communicate with each other, and are adjacent and parallel to each other.

As illustrated in FIG. 1, the aspiration flow passage 11*a* extends from an aspiration port 11*a*1 located at a distal end portion of the catheter body 11 to a communication port located at a proximal end portion of the catheter body 11 and connected to an in-hub flow passage of the hub 12.

As illustrated in FIG. 1, the guide wire insertion hole 11*b* extends from a distal opening 11*b*1 on the distal side to a proximal opening 11*b*2 on the proximal side. The guide wire insertion hole 11*b* is of a so-called rapid exchange type, and is formed along only a part of the distal side of the aspiration flow passage 11*a*. That is, the proximal opening 11*b*2 of the guide wire insertion hole 11*b* is located on the distal side with respect to the communication port of the aspiration flow passage 11*a*.

The aspiration port 11*a*1 of the present embodiment is formed on a distal end surface of the catheter body 11. The aspiration port 11*a*1 of the present embodiment is formed on the distal end surface inclined with respect to the longitudinal direction A of the catheter body 11, but is not limited to this configuration. The aspiration port 11*a*1 may be formed on the distal end surface orthogonal to the longitudinal direction A.

A peripheral wall surrounding the guide wire insertion hole 11*b* of the present embodiment includes a coil tube made of an X-ray contrast metal. The coil tube is made of an X-ray or radiation opaque material such as gold or platinum. Therefore, the position of the distal end of the catheter body 11 in the living body can be visualized by X-ray imaging.

As a material for forming the catheter body 11, a polymer material such as polyolefin (for example, polyethylene, polypropylene, polybutene, an ethylene-propylene copolymer, an ethylene-vinyl acetate copolymer, an ionomer, a mixture of two or more thereof, or the like), polyolefin elastomer, crosslinked polyolefin, polyvinyl chloride, polyamide, polyamide elastomer, polyester, polyester elastomer, polyurethane, polyurethane elastomer, a fluororesin, polycarbonate, polystyrene, polyacetal, polyimide, polyetherimide, polyetheretherketone, or a mixture thereof can be used.

The hub 12 and the covering tube 13 are attached to the proximal side of the catheter body 11 of the present embodiment.

The proximal end of the catheter body 11 is connected to the distal end of the hub 12. The aspiration device 2 is connected to the proximal end of the hub 12 directly or via a medical tube 80. The in-hub flow passage of the hub 12 liquid-tightly communicates with the aspiration flow passage 11*a* of the catheter body 11. Furthermore, the in-hub flow passage of the hub 12 is liquid-tightly connected to the aspiration device 2 directly or via the medical tube 80 for example, through a Luer-lock-type connector portion.

Examples of a material for forming the hub 12 include various resin materials such as polyolefin such as polyethylene, polypropylene, or an ethylene-propylene copolymer; an ethylene-vinyl acetate copolymer (EVA); polyvinyl chloride; polyvinylidene chloride; polystyrene; polyamide; polyimide; polyamideimide; polycarbonate; poly-(4-methylpentene-1); an ionomer; an acrylic resin; polymethyl methacrylate; an acrylonitrile-butadiene-styrene copolymer (ABS resin); an acrylonitrile-styrene copolymer (AS resin); a butadiene-styrene copolymer; polyester such as polyethylene terephthalate (PET), polybutylene terephthalate (PBT), or polycyclohexane terephthalate (PCT); polyether; polyetherketone (PEK); polyetheretherketone (PEEK); polyetherimide; polyacetal (POM); polyphenylene oxide; modified polyphenylene oxide; polysulfone; polyether sulfone; polyphenylene sulfide; polyarylate; aromatic polyester (liquid crystal polymer); polytetrafluoroethylene, polyvinylidene fluoride, other fluorine-based resins; and the like. Furthermore, a blend or a polymer alloy, which contains one or more of these materials, may be used. In addition, various glass materials, various ceramic materials, and various metal materials may be used.

As illustrated in FIG. 1, the covering tube 13 covers the proximal end of the catheter body 11. More specifically, the covering tube 13 of the present embodiment covers the proximal end of the catheter body 11 so as to cover both a portion inserted into the hub 12 and a portion not inserted into the hub 12 on the distal side of the portion in the proximal end of the catheter body 11. By providing such a covering tube 13, it is possible to prevent a kink from occurring at a connection portion between the catheter body 11 and the hub 12. Examples of a material for forming the covering tube 13 include the same materials as the above-described formation materials exemplified as the materials for forming the catheter body 11.

The balloon 14 is attached on the outer surface of the catheter body 11 and is inflatable radially outward of the catheter body 11 by receiving supply of a fluid such as liquid. When the balloon 14 inflates and comes into contact with the inner wall of the blood vessel BV, the position of the catheter body 11 in the blood vessel BV can be determined.

As illustrated in FIG. 1, the aspiration device 2 can be connected to the aspiration catheter 1. The aspiration device 2 of the present embodiment is connected to the hub 12 of the aspiration catheter 1 via the medical tube 80, but is not limited to this configuration. The aspiration device 2 may be directly connected to the aspiration catheter 1. The aspiration device 2 can generate a negative pressure in the aspiration catheter 1 in a state of being connected to the aspiration catheter 1.

As illustrated in FIG. 1, the aspiration device 2 of the present embodiment includes a controller 21, a memory 22, an input/output interface 23, and an aspiration pump 24.

The controller 21 includes one or more processors. The controller 21 may include a dedicated processor specialized in processing of controlling the operation of the aspiration pump 24, communicating with the X-ray image processing device 3*a* and the ultrasound image processing device 3*b* via the input/output interface 23, and acquiring length information and flow passage diameter information regarding a lesion Z in the blood vessel BV based on image data acquired from the X-ray image processing device 3*a* and the ultrasound image processing device 3*b*. The controller 21 may be a general-purpose processor such as a central processing unit (CPU). The controller 21 may include one or more dedicated circuits, or one or more processors and one or more dedicated circuits. The dedicated circuit is, for example, a field-programmable gate array (FPGA) or an application specific integrated circuit (ASIC). The controller 21 executes information processing related to operation of the aspiration device 2 while controlling each unit of the aspiration device 2.

The memory 22 includes, for example, a random access memory (RAM) and a read only memory (ROM). The memory 22 may function as, for example, a main storage device or a cache memory that stores image data acquired from the X-ray image processing device 3*a* and the ultrasound image processing device 3*b*. The memory 22 stores any information used for the operation of the aspiration device 2, for example, an aspiration operation program for each aspiration mode of the aspiration pump 24. In addition, the memory 22 may further store a system program, an application program, various types of information received by the input/output interface 23.

The input/output interface 23 is an interface circuit that inputs and outputs signals to and from the X-ray image processing device 3a and the ultrasound image processing device 3b. The aspiration device 2 of the present embodiment acquires X-ray image data from the X-ray image processing device 3a via the input/output interface 23. Furthermore, the aspiration device 2 of the present embodiment acquires ultrasound image data from the ultrasound image processing device 3b via the input/output interface 23. The input/output interface 23 may include at least one of a universal serial bus (USB) interface, a wireless local area network (LAN) interface, a wireless communication interface such as a Bluetooth interface, and a wired communication interface. Moreover, the input/output interface 23 may include at least one of a touch panel, a button, a light emitting diode (LED), and a buzzer, as a user interface to the operator.

The aspiration pump 24 can generate negative pressure in the aspiration catheter 1, and the operation of the aspiration pump 24 is controlled by the controller 21. That is, the controller 21 controls aspiration of the aspiration pump 24. The controller 21 can control, for example, the aspiration pressure, aspiration time, aspiration period, and the like of the aspiration pump 24. Details will be described later, and the controller 21 of the present embodiment controls the aspiration pressure, aspiration time, and aspiration period in the aspiration catheter 1 by controlling the aspiration pump 24 based on the length information and flow passage diameter information regarding the lesion Z in the blood vessel By.

The X-ray image processing device 3a as the imaging device 3 can image the contrasted blood vessel BV from the outside of the living body. The X-ray image processing device 3a of the present embodiment includes a controller 31a, a memory 32a, an input/output interface 33a, and an imaging unit 34a.

The controller 31a includes one or more processors. The controller 31a may include a dedicated processor specialized in processing of controlling the operation of the imaging unit 34a and communicating with the aspiration device 2 via the input/output interface 33a. The controller 31a may include a general-purpose processor such as a CPU. The controller 31a may include one or more dedicated circuits, or one or more processors and one or more dedicated circuits. The dedicated circuit is, for example, an FPGA or an ASIC. The controller 31a executes information processing related to the operation of the X-ray image processing device 3a while controlling each unit of the X-ray image processing device 3a.

The memory 32a includes, for example, a RAM and a ROM. The memory 32a may function as, for example, a main storage device or a cache memory that stores X-ray image captured by the imaging unit 34a. The memory 32a stores any information used for the operation of the X-ray image processing device 3a. In addition, the memory 32a may further store a system program, an application program, various types of information received by the input/output interface 33a.

The input/output interface 33a is an interface circuit that inputs and outputs signals to and from the aspiration device 2. The X-ray image processing device 3a of the present embodiment can transmit the X-ray image data to the aspiration device 2 via the input/output interface 33a. Moreover, the X-ray image processing device 3a may output the X-ray image captured by the imaging unit 34a to a display or the like via the input/output interface 33a according to an instruction of the controller 31a. The input/output interface 33a may include at least one of a USB interface, a wireless LAN interface, a wireless communication interface such as a Bluetooth interface, and a wired communication interface. Moreover, the input/output interface 33a may include at least one of a touch panel, a button, an LED, and a buzzer, a user interface to the operator.

The imaging unit 34a irradiates the living body with an X-ray from the outside of the living body of a patient to acquire the X-ray image of the lesion Z of the blood vessel BV. FIG. 2A is a view illustrating an example of the X-ray image acquired by the imaging unit 34a. The imaging unit 34a can acquire the X-ray image of the blood vessel BV as illustrated in FIG. 2A by causing a contrast agent to flow into the blood vessel BV. FIG. 2A illustrates, as an example, a state in which there is a lesion Z reduced in diameter by a foreign substance such as thrombus Y (see FIG. 1) in a part of the imaged blood vessel By. Details will be described later, and the controller 21 of the aspiration device 2 of the present embodiment can extract length information and flow passage diameter information regarding the lesion Z in the blood vessel BV based on the X-ray image acquired by the imaging unit 34a as illustrated in FIG. 2A.

The ultrasound image processing device 3b as the imaging device 3 can image the blood vessel BV from the inside of the blood vessel BV by ultrasound. The ultrasound image processing device 3b of the present embodiment includes a controller 31b, a memory 32b, an input/output interface 33b, an ultrasound catheter 4, and a motor drive unit 5.

The controller 31b includes one or more processors. The controller 31b may include a dedicated processor specialized in processing of controlling the operation of the motor drive unit 5 supporting the ultrasound catheter 4, generating an ultrasound image based on ultrasound data acquired from the ultrasound catheter 4, and communicating with the aspiration device 2 via the input/output interface 33b. The controller 31b may include a general-purpose processor such as a CPU. The controller 31b may include one or more dedicated circuits, or one or more processors and one or more dedicated circuits. The dedicated circuit is, for example, an FPGA or an ASIC. The controller 31b executes information processing related to the operation of the ultrasound image processing device 3b while controlling each unit of the ultrasound image processing device 3b.

The memory 32b includes, for example, a RAM and a ROM. The memory 32b may function as, for example, a main storage device or a cache memory that stores ultrasound data acquired from the ultrasound catheter 4, ultrasound image data generated by the controller 31b based on the ultrasound data, and the like. The memory 32b stores any information used for the operation of the ultrasound image processing device 3b. In addition, the memory 32b may further store a system program, an application program, various types of information received by the input/output interface 33b.

The input/output interface 33b is an interface circuit that inputs and outputs signals to and from the aspiration device 2. The ultrasound image processing device 3b of the present embodiment can transmit the ultrasound image data to the aspiration device 2 via the input/output interface 33b. Moreover, the ultrasound image processing device 3b may output the ultrasound image generated by the controller 31b to a display or the like via the input/output interface 33b. The input/output interface 33b may include at least one of a USB interface, a wireless LAN interface, a wireless communication interface such as a Bluetooth interface, and a wired communication interface. Moreover, the input/output interface 33*b* may include at least one of a touch panel, a button, an LED, and a buzzer, as a user interface to the operator.

Figure 2B:
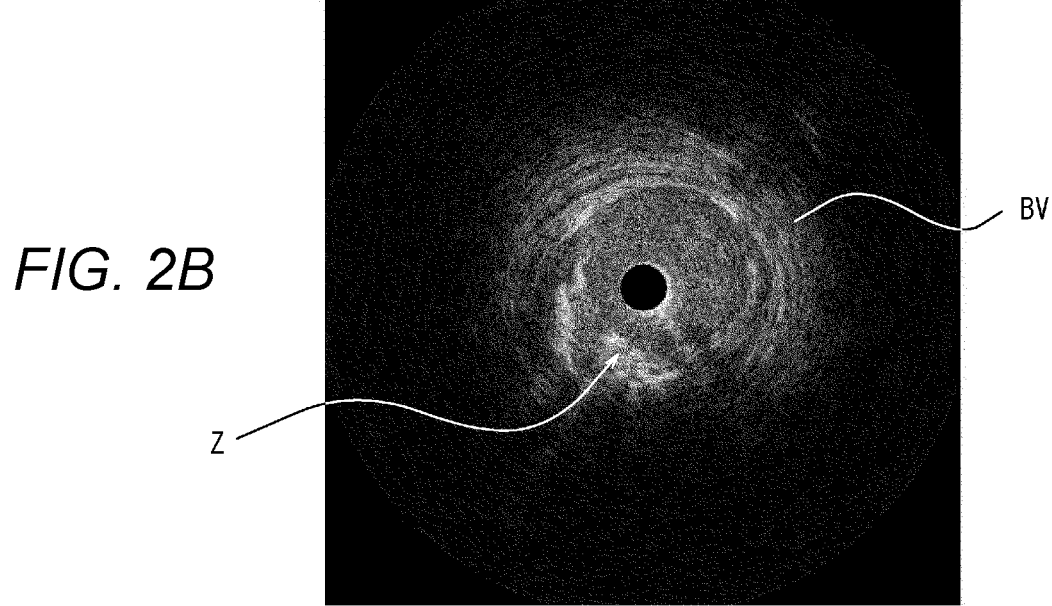
FIG. 2B is a view illustrating an example of an ultrasound image generated by an ultrasound image processing device.

As described above, in the ultrasound image processing device 3*b* of the present embodiment, the controller 31*b* controls the operation of the motor drive unit 5 and acquires ultrasound data from the ultrasound catheter 4. The ultrasound catheter 4 includes an imaging unit capable of transmitting and receiving ultrasound therein. The proximal end of the ultrasound catheter 4 is connected to the motor drive unit 5. The motor drive unit 5 can move the imaging unit of the ultrasound catheter 4 along the longitudinal direction according to an instruction from the controller 31*b* of the ultrasound image processing device 3*b*. Furthermore, the motor drive unit 5 can rotate the imaging unit of the ultrasound catheter 4 according to the instruction from the controller 31*b* of the ultrasound image processing device 3*b*. That is, the imaging unit of the ultrasound catheter 4 moves in the longitudinal direction along the blood vessel BV while rotating in the blood vessel BV, and acquires ultrasound data in the blood vessel By. The controller 31*b* of the ultrasound image processing device 3*b* generates ultrasound image data in the blood vessel BV based on the ultrasound data. FIG. 2B is a view illustrating an example of the ultrasound image generated by the controller 31*b*. FIG. 2B illustrates, as an example, a state in which there is the lesion Z reduced in diameter by the foreign substance such as thrombus Y (see FIG. 1) in a part of the imaged blood vessel By. Details will be described later, and the controller 21 of the aspiration device 2 of the present embodiment can acquire length information and flow passage diameter information regarding the lesion Z in the blood vessel BV based on the ultrasound image in the blood vessel BV, which is generated based on the ultrasound data acquired from the ultrasound catheter 4 as illustrated in FIG. 2B.

Figure 3:
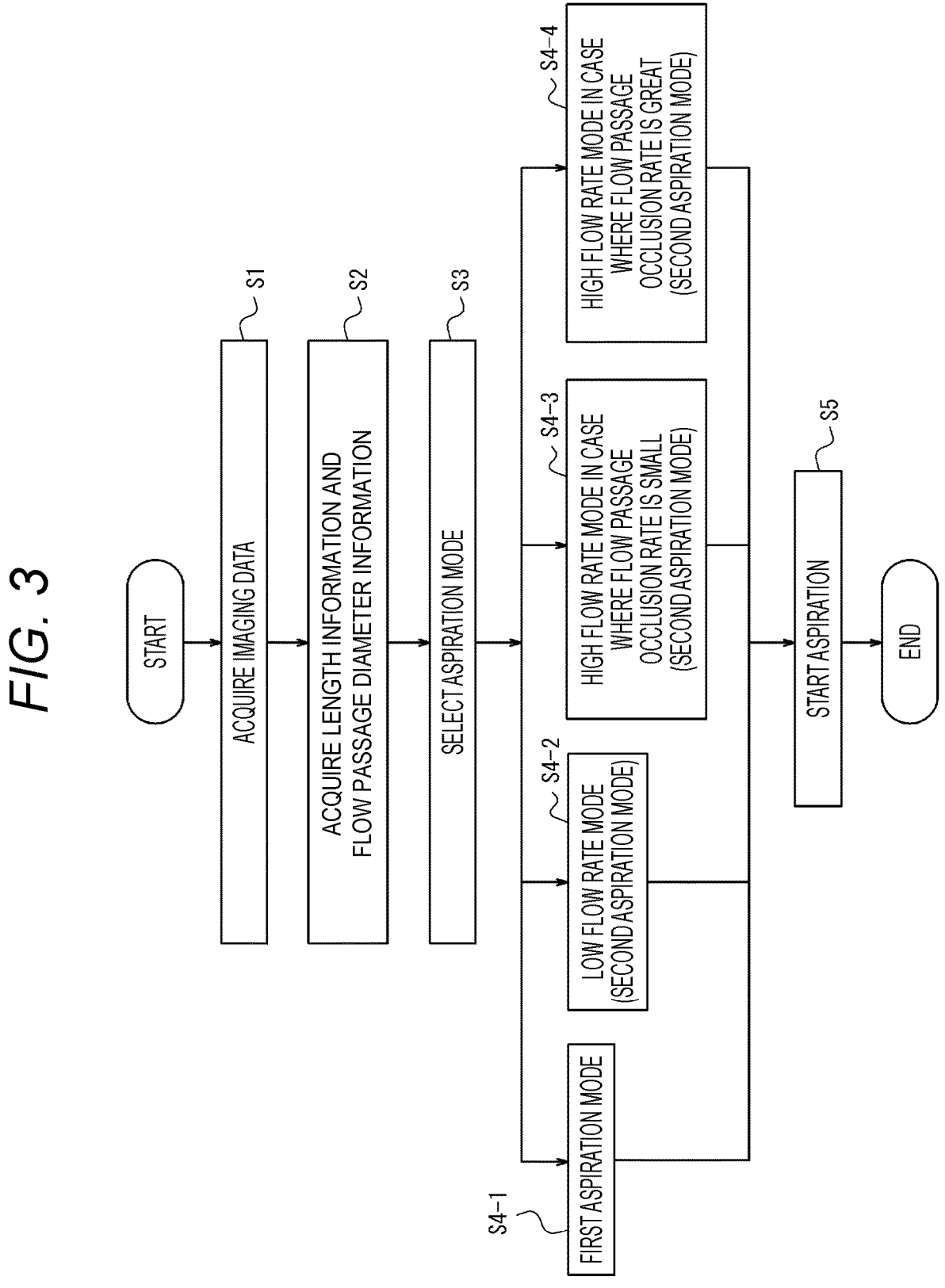
FIG. 3 is a flowchart of a process performed by an aspiration device according to an embodiment.
Figure 4:
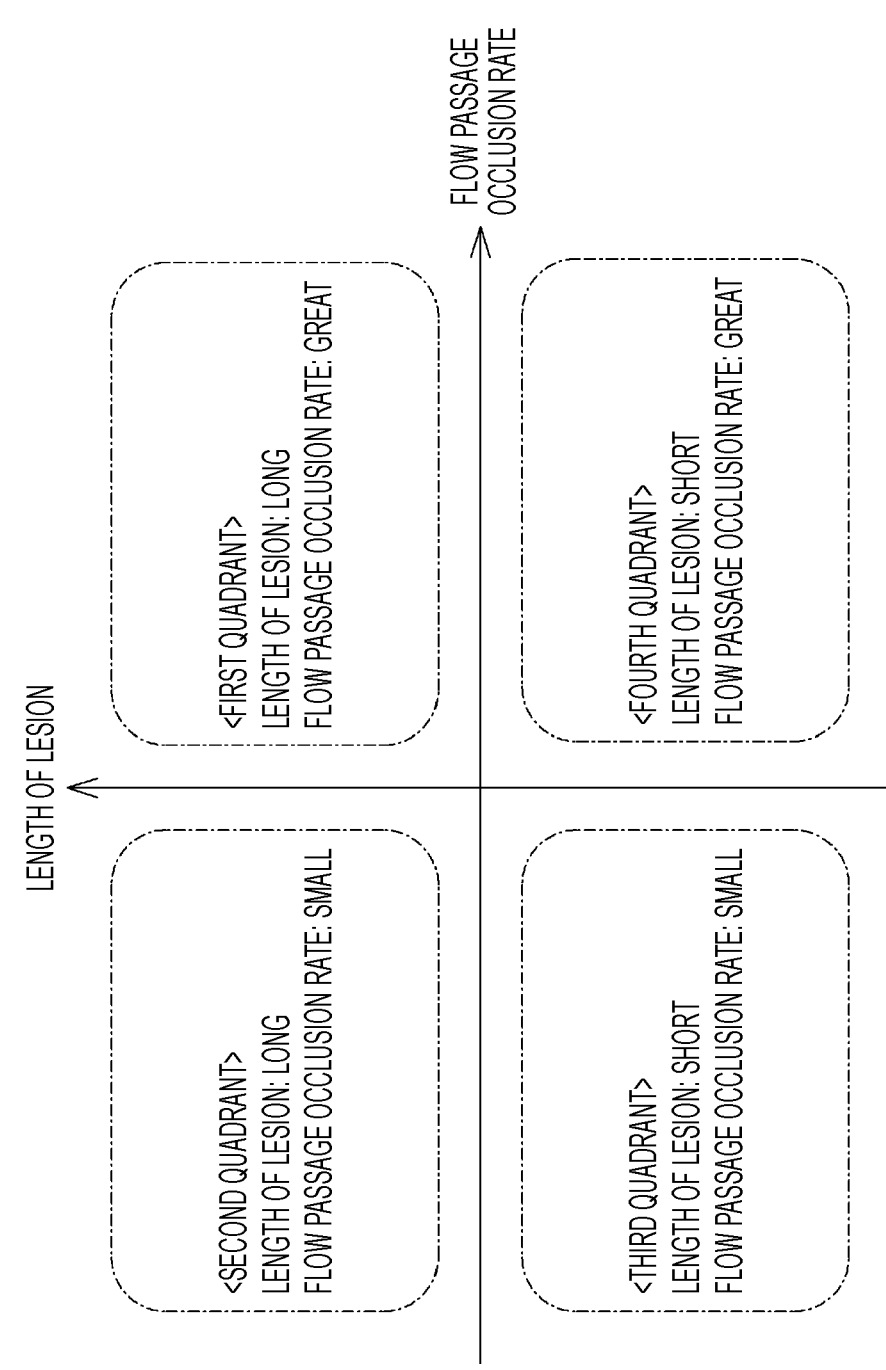
FIG. 4 is a diagram illustrating four states of a lesion that can be specified by the aspiration device.
Figure 6A:
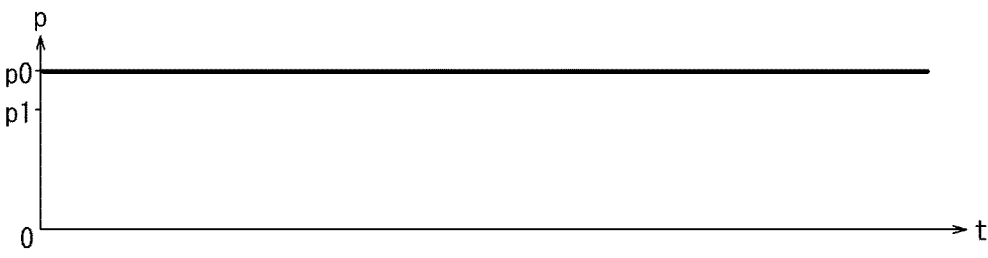
FIG. 6A is a diagram illustrating an example of aspiration control executed in a case where the state of the specified lesion belongs to the third quadrant of FIG. 4.
Figure 6B:
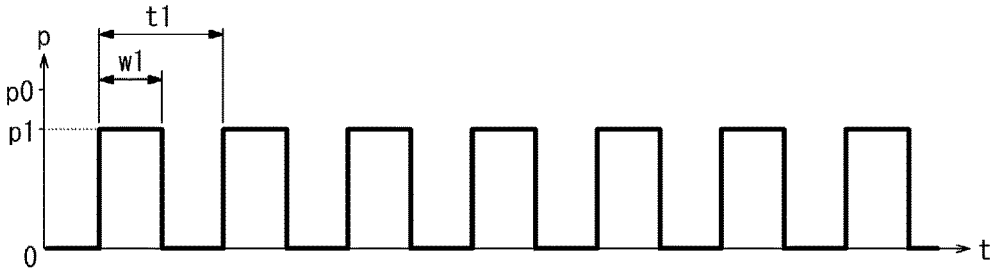
FIG. 6B is a diagram illustrating an example of aspiration control executed in a case where the state of the specified lesion belongs to the fourth quadrant of FIG. 4.
Figure 6C:
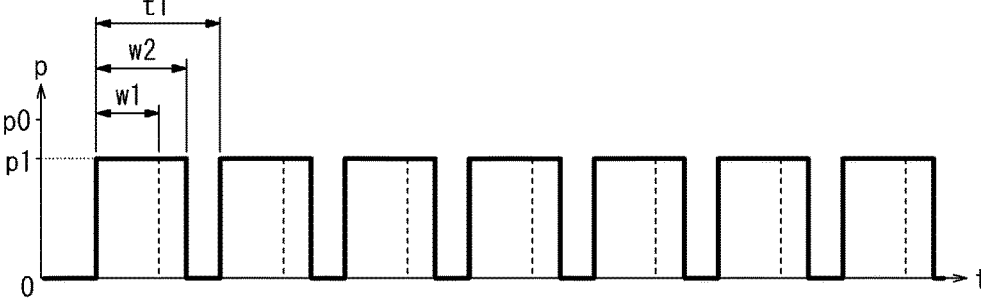
FIG. 6C is a diagram illustrating an example of aspiration control executed in a case where the state of the specified lesion belongs to the second quadrant of FIG. 4.
Figure 6D:
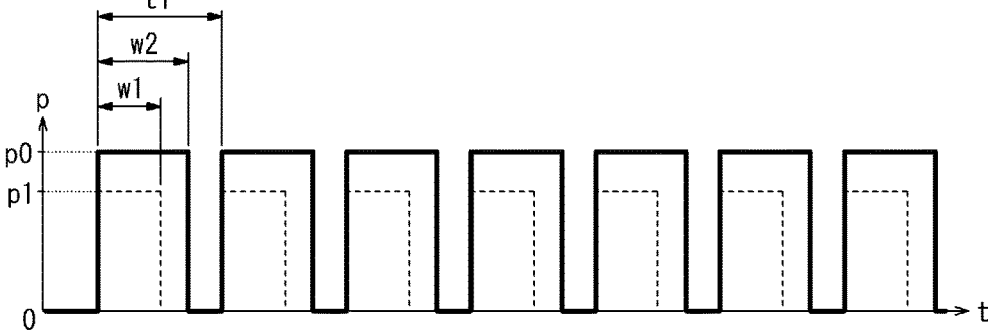
FIG. 6D is a diagram illustrating an example of aspiration control executed in a case where the state of the specified lesion belongs to the first quadrant of FIG. 4.

Next, details of the aspiration control of the aspiration catheter 1 by the aspiration device 2 will be described with reference to FIGS. 1 to 6. FIG. 3 is a flowchart of a process performed by the controller 21 of the aspiration device 2. FIG. 4 is a diagram illustrating four states of the lesion Z that can be specified by the controller 21. FIG. 5 is a diagram illustrating an example of the aspiration control by the controller 21 according to the state of the specified lesion Z. FIG. 6A is a diagram illustrating an example of the aspiration control executed in a case where the state of the lesion Z belongs to a third quadrant of FIG. 4. FIG. 6B is a diagram illustrating an example of the aspiration control executed in a case where the state of the lesion Z belongs to a fourth quadrant of FIG. 4. FIG. 6C is a diagram illustrating an example of the aspiration control executed in a case where the state of the lesion Z belongs to a second quadrant of FIG. 4. FIG. 6D is a diagram illustrating an example of the aspiration control executed in a case where the state of the lesion Z belongs to a first quadrant of FIG. 4. In FIGS. 6A to 6D, the horizontal axis represents time t, and the vertical axis represents aspiration pressure p.

As illustrated in FIG. 3, the controller 21 of the aspiration device 2 acquires imaging data (S1 in FIG. 3). In the present embodiment, the controller 21 acquires X-ray image data from the X-ray image processing device 3*a*. Furthermore, the controller 21 acquires ultrasound image data from the ultrasound image processing device 3*b*.

In the present embodiment, before the aspiration catheter 1 is inserted into the blood vessel BV, an X-ray image of the lesion Z is captured by the X-ray image processing device 3*a* (see FIG. 2A) and an ultrasound image of the lesion Z is captured by the ultrasound image processing device 3*b* (see FIG. 2B). The X-ray image of the lesion Z may be continuously captured by the X-ray image processing device 3*a* (see FIG. 2A) in a state in which the aspiration catheter 1 is inserted into the blood vessel BV as illustrated in FIG. 1. The X-ray image data and ultrasound image data of the lesion Z are transmitted to the aspiration device 2.

The controller 21 of the aspiration device 2 acquires length information and flow passage diameter information regarding the lesion Z in the blood vessel BV based on the X-ray image data and the ultrasound image data which are respectively acquired from the X-ray image processing device 3*a* and the ultrasound image processing device 3*b* (S2 in FIG. 3). For example, the controller 21 analyzes the X-ray image illustrated in FIG. 2A to specify a lesion Z reduced in diameter by the foreign substance such as thrombus Y (see FIG. 1) in the blood vessel By. Then, the controller 21 acquires length information and flow passage diameter information regarding the specified lesion Z. The length information only needs to be capable of specifying the entire length of the lesion Z in an extending direction of the blood vessel BV, and may indicate, for example, a length L (see FIG. 1) itself of the lesion Z in the extending direction of the blood vessel By. The flow passage diameter information only needs to be capable of specifying a narrowing state of the flow passage of the lesion Z, and may be, for example, the degree of occlusion of the flow passage of the blood vessel BV at the lesion Z (hereinafter, simply referred to as a "flow passage occlusion rate"). The flow passage occlusion rate may be, for example, a narrowing degree of a normal flow passage DO (see FIG. 1) at the lesion Z, which is estimated from the flow passage diameter before and after the lesion Z.

Next, the controller 21 selects an aspiration operation of the aspiration catheter 1 based on the acquired length information and flow passage diameter information regarding the lesion Z (S3 in FIG. 3). Specifically, the controller 21 of the present embodiment selects an aspiration operation of the aspiration catheter 1 by comparing each of the length L of the lesion Z and the flow passage occlusion rate, which are acquired from the image data, with a preset threshold.

The controller 21 selects either a first aspiration mode or a second aspiration mode based on the length information and flow passage diameter information regarding the lesion Z in the blood vessel By. As illustrated in FIG. 6A, in the first aspiration mode, the inside of the aspiration catheter 1 is maintained at a constant aspiration pressure. As illustrated in FIGS. 6B to 6D, in the second aspiration mode, the magnitude of the aspiration pressure in the aspiration catheter 1 continuously varies. By the first aspiration mode and the second aspiration mode, it is easy to select an appropriate aspiration operation corresponding to the state of the lesion Z.

More specifically, the controller 21 of the present embodiment selects the first aspiration mode in a case where the length L of the lesion Z is equal to or less than a predetermined value (hereinafter, referred to as a "length threshold") as a threshold and the flow passage occlusion rate at the lesion Z is equal to or less than a predetermined value (hereinafter, referred to as a "occlusion threshold") as a threshold (S4-1 in FIG. 3). That is, as illustrated in FIG. 6A, the controller 21 performs aspiration control so as to maintain a constant aspiration pressure p0. In other words, the controller 21 selects the first aspiration mode in a case where the state of the lesion Z is determined to be a state in the third quadrant illustrated in FIG. 4. Here, the length threshold of the present embodiment is set to 7 mm as an example, but is not limited to this numerical value, and the length threshold can be set as appropriate. Furthermore, the occlusion threshold of the present embodiment is set to 50% as an example, but is not limited to this numerical value, and the occlusion threshold can be set as appropriate. FIG. 5 illustrates, as an example of the lesion Z determined to be in the state in the third quadrant, the lesion Z of which the length L is 3 mm and the flow passage occlusion rate is 30%.

On the other hand, the controller 21 selects the second aspiration mode in any of the following cases (1) to (3).

(1) A case where the length L of the lesion Z is greater than the length threshold (e.g., 7 mm), and the flow passage occlusion rate at the lesion Z is equal to or less than the occlusion threshold (e.g., 50%).

(2) A case where the length L of the lesion Z is equal to or less than the length threshold (e.g., 7 mm), and the flow passage occlusion rate at the lesion Z is greater than the occlusion threshold (e.g., 50%).

(3) A case where the length L of the lesion Z is greater than the length threshold (e.g., 7 mm), and the flow passage occlusion rate at the lesion Z is greater than the occlusion threshold (e.g., 50%).

The case of (1) described above means a case where the state of the lesion Z is in the second quadrant of FIG. 4. The case of (2) described above means a case where the state of the lesion Z is in the fourth quadrant of FIG. 4. The case of (3) described above means a case where the state of the lesion Z is in the first quadrant of FIG. 4.

As described above, in the present embodiment, when at least one of the case where the length L of the lesion Z is greater than 7 mm and the case where the flow passage occlusion rate at the lesion Z is greater than 50% is satisfied, the controller 21 selects the second aspiration mode. That is, as illustrated in FIGS. 6B to 6D, the controller 21 performs aspiration control so as to repeatedly vary the magnitude of the aspiration pressure. In other words, the controller 21 selects the second aspiration mode in a case where the state of the lesion Z is determined to be a state in any of the first quadrant, second quadrant, and fourth quadrant illustrated in FIG. 4. When the second aspiration mode in which the magnitude of the aspiration pressure is repeatedly varied is selected, deformation or destruction of the foreign substance such as the thrombus Y on the inner wall of the blood vessel BV (see FIG. 1) is likely to occur as compared with the case where the first aspiration mode is selected. Therefore, the aspiration efficiency for the foreign substance can be increased. Furthermore, in the present embodiment, a blood flow is blocked by the balloon 14 (see FIG. 1), and the blood vessel BV repeats inflation and deflation by performing pulse aspiration in the second aspiration mode. Therefore, deformation and destruction of the foreign substance such as the thrombus Y (see FIG. 1) can be promoted, and the foreign substance can be more efficiently removed.

Moreover, in the cases (1) to (3) described above, the controller 21 of the present embodiment controls the fluctuation of the aspiration pressure in the second aspiration mode based on the length information and flow passage diameter information.

Specifically, the second aspiration mode of the present embodiment includes a low flow rate mode and a high flow rate mode in which the aspiration flow rate per minute is different. The "low flow rate mode" described herein means a mode in which the aspiration flow rate per minute is relatively low in two modes having different aspiration flow rates per minute in the second aspiration mode, and the "high flow rate mode" means a mode in which the aspiration flow rate per minute is relatively high. In a case where the length L of the lesion Z is greater than the length threshold (e.g., 7 mm) and the flow passage occlusion rate at the lesion Z is equal to or less than the occlusion threshold (e.g., 50%), the controller 21 of the present embodiment selects the high flow rate mode in the second aspiration mode based on the length information and the flow passage diameter information (see S4-3 in FIG. 3). In other words, the controller 21 of the present embodiment selects the high flow rate mode in the second aspiration mode in a case where the state of the lesion Z is determined to be a state in the second quadrant illustrated in FIG. 4. FIG. 5 illustrates, as an example of the lesion Z determined to be in the state in the second quadrant, the lesion Z of which the length L is 15 mm and the flow passage occlusion rate is 30%. As indicated by a solid line in FIG. 6C, in the high flow rate mode, an aspiration period t1 equal to that of the low flow rate mode indicated by a broken line in FIG. 6C is set, and an aspiration time w2 in one aspiration period t1 is longer than an aspiration time w1 in one aspiration period t1 of the low flow rate mode. Therefore, as compared with the low flow rate mode, in the high flow rate mode, the aspiration flow rate per minute is controlled to be increased.

As described above, in a case where the length L of the lesion Z is long (in the present embodiment, in a case of belonging to the first quadrant or the second quadrant in FIG. 4), by using the second aspiration mode, the deformation, destruction, and the like of the foreign substance such as the thrombus Y (see FIG. 1) can be promoted, and the aspiration efficiency can be increased. Here, it is not preferable that the blood flow rate in the blood vessel BV rapidly changes before and after the foreign substance such as the thrombus Y (see FIG. 1) is removed in the blood vessel By. Such a rapid change in the blood flow rate is likely to occur when the foreign substance at the lesion Z having a large flow passage occlusion rate is removed. However, in a case where the state of the lesion Z is determined to be a state of the second quadrant illustrated in FIG. 4, the flow passage occlusion rate at the lesion Z is not great, and thus the above-described rapid change in the blood flow rate is unlikely to occur before and after the removal of the foreign substance. Therefore, in a case where the state of the lesion Z is determined to be a state in the second quadrant illustrated in FIG. 4, the controller 21 of the present embodiment selects the high flow rate mode having a high aspiration flow rate per minute as described above instead of the low flow rate mode having a low aspiration flow rate per minute.

On the other hand, in a case where the length L of the lesion Z is equal to or less than the length threshold (e.g., 7 mm) and the flow passage occlusion rate at the lesion Z is greater than the occlusion threshold (e.g., 50%), the controller 21 of the present embodiment selects the low flow rate mode in the second aspiration mode (S4-2 in FIG. 3). In other words, the controller 21 of the present embodiment selects the low flow rate mode in the second aspiration mode in a case where the state of the lesion Z is determined to be a state in the fourth quadrant illustrated in FIG. 4. FIG. 5 illustrates, as an example of the lesion Z determined to be in the state in the fourth quadrant, the lesion Z of which the length L is 5 mm and the flow passage occlusion rate is 85%.

As described above, in a case where the length L of the lesion Z is short and the flow passage occlusion rate at the lesion Z is great (in the present embodiment, in a case of belonging to the fourth quadrant in FIG. 4), by using the second aspiration mode, the deformation, destruction, and the like of the foreign substance such as the thrombus Y (see FIG. 1) can be promoted, and the aspiration efficiency can be increased. However, a rapid change in the blood flow rate is likely to occur before and after the foreign substance is removed. Thus, the controller 21 of the present embodiment selects the low flow rate mode having the low aspiration flow rate per minute in a case where the state of the lesion Z is determined to be a state in the fourth quadrant illustrated in FIG. 4. Therefore, the foreign substance is gradually aspirated, and a rapid change in the blood flow rate can be suppressed.

Moreover, in a case where the length L of the lesion Z is greater than the length threshold (e.g., 7 mm) and the flow passage occlusion rate at the lesion Z is greater than the occlusion threshold (e.g., 50%), the controller 21 of the present embodiment selects the high flow rate mode in the second aspiration mode (S4-4 in FIG. 3). In other words, the controller 21 of the present embodiment selects the high flow rate mode in the second aspiration mode in a case where the state of the lesion Z is determined to be a state in the first quadrant illustrated in FIG. 4. FIG. 5 illustrates, as an example of the lesion Z determined to be in the state in the first quadrant, the lesion Z of which the length L is 20 mm and the flow passage occlusion rate is 70%.

As described above, in a case where the length L of the lesion Z is long and the flow passage occlusion rate at the lesion Z is great (in the present embodiment, in a case of belonging to the first quadrant in FIG. 4), by using the second aspiration mode, the deformation, destruction, and the like of the foreign substance such as the thrombus Y (see FIG. 1) can be promoted, and the aspiration efficiency can be increased. As described above, in a case where the flow passage occlusion rate at the lesion Z is great, a rapid change in the blood flow rate is likely to occur before and after the removal of the foreign substance. Therefore, from this viewpoint, the low flow rate mode is preferable. However, in a case where the length L of the lesion Z is long, it is more preferable to remove the foreign substance and recover the normal blood flow as soon as possible. Therefore, in a case where the state of the lesion Z is determined to be a state in the first quadrant illustrated in FIG. 4, the controller 21 of the present embodiment selects the high flow rate mode having a high aspiration flow rate per minute rather than selecting the low flow rate mode having a low aspiration flow rate per minute.

In the present embodiment, the high flow rate mode selected in a case where the state of the lesion Z belongs to the first quadrant in FIG. 4 is the same as the high flow rate mode selected in a case where the state of the lesion Z belongs to the second quadrant in FIG. 4, but the present disclosure is not limited to this configuration. The second aspiration mode may further include another mode in which the aspiration flow rate per minute is higher than that in the above-described high flow rate mode. That is, the second aspiration mode may include three or more modes having different aspiration flow rates per minute. In such cases, in a case where the length L of the lesion Z is greater than the length threshold (e.g., 7 mm) and the flow passage occlusion rate at the lesion Z is greater than the occlusion threshold (e.g., 50%), the controller 21 may select another mode in which the aspiration flow rate per minute is higher than those of the above-described low flow rate mode and high flow rate mode in the second aspiration mode. In this manner, it is easy to achieve the rapid removal of the foreign substance. As illustrated in FIG. 6D, in such another mode, for example, the aspiration pressure p0 is caused to be larger than the aspiration pressure p1 in the high flow rate mode even when the aspiration time w2 in the aspiration period t1 and one aspiration period t1 is caused to be the same as that in the high flow rate mode described above. Therefore, as compared with the high flow rate mode described above, in this another mode, the aspiration flow rate per minute is increased.

The controller 21 of the present embodiment may determine the maximum aspiration pressure in the second aspiration mode based on at least one of hardness information of the normal portion of the blood vessel BV and hardness information of the thrombus Y at the lesion Z of the blood vessel BV (see FIG. 1). That is, the controller 21 may determine the maximum aspiration pressure corresponding to the aspiration flow rate per minute in the second aspiration mode based on at least one of hardness information of the normal portion of the blood vessel BV and hardness information of the thrombus Y at the lesion Z of the blood vessel BV (see FIG. 1). For example, the controller 21 may determine the degree of deformation of the blood vessel BV in the vicinity of the lesion Z, and determine the maximum aspiration pressure to be used in the second aspiration mode based on the determination result by, for example, selecting from a plurality of options. For example, the controller 21 gradually increases the aspiration pressure of the aspiration catheter 1 and measures the degree of deformation of the inner wall of the normal blood vessel By. Then, in a case where the degree of deformation increases at a predetermined aspiration pressure p, the controller 21 may determine the aspiration pressure p as the maximum aspiration pressure at the time of aspiration at the lesion Z. On the other hand, in a case where the degree of deformation does not increase even when the aspiration pressure is increased, the controller 21 may determine the aspiration pressure p0 described above (See FIG. 6A and FIG. 6D) as the maximum aspiration pressure at the time of the aspiration at the lesion Z. In this manner, the controller 21 may control the aspiration pressure used in the second aspiration mode by determining the degree of deformation as the hardness information of the normal portion of the blood vessel By. Furthermore, the maximum aspiration pressure in the second aspiration mode may be determined based on change information of the aspiration pressure in the aspiration catheter 1. Specifically, the aspiration pressure in the aspiration flow passage 11a of the aspiration catheter 1 may be measured, an inflection point at which the temporal change rate of the pressure change rapidly increases may be obtained, and a value near this value may be set as the maximum aspiration pressure. This inflection point correlates with a point at which the degree of deformation increases.

Furthermore, the controller 21 may determine the maximum aspiration pressure in the second aspiration mode based on the hardness information of the thrombus Y at the lesion Z of the blood vessel BV (see FIG. 1). The hardness of the thrombus Y at the lesion Z of the blood vessel BV only needs to be obtained by measuring a reaction force when the distal end of the guide wire is brought into contact with the thrombus Y at the lesion Z under a certain condition (for example, pressing the distal end of the guide wire against the thrombus Y at a certain speed). The controller 21 may determine the maximum aspiration pressure according to the reaction force.

The control unit 21 of the present embodiment uses different aspiration flow rates per minute between the low flow rate mode and the high flow rate mode in the second aspiration mode described above by varying the aspiration time (see "w1" and "w2" in FIG. 6C) in one aspiration period, but the aspiration flow rate per minute may be varied by varying the aspiration pressure. That is, the controller 21 may control the aspiration pressure in the second aspiration mode based on the length information and flow passage diameter information regarding the lesion Z, and according to this or separately from this, may control the aspiration pressure in the second aspiration mode based on at least one of the hardness information of the normal portion of the blood vessel BV or the hardness information of the thrombus Y at the lesion Z of the blood vessel BV.

In this manner, after an aspiration control method for the aspiration catheter 1 by the controller 21 is determined, the aspiration control is executed through the aspiration catheter 1 inserted into the blood vessel BV (S5 in FIG. 3).

The aspiration device and the aspiration system according to the present disclosure are not limited to the specific configuration and processing indicated in the above-described embodiment, and various modifications and changes can be made without departing from the scope of the claims.

The aspiration system 100 described above includes, as the imaging device 3, the X-ray image processing device 3a and the ultrasound image processing device 3b, but is not limited to this configuration. As long as the aspiration device 2 can acquire the length information and flow passage diameter information regarding the lesion Z of the blood vessel BV, the acquisition method is not particularly limited. Therefore, one of the X-ray image processing device 3a and the ultrasound image processing device 3b may be provided, or another imaging device 3 may be provided. However, image data of the lesion Z can be easily acquired by using the X-ray image processing device 3a. Furthermore, as in the above-described embodiment, by using the ultrasound image processing device 3b in addition to the X-ray image processing device 3a, the specification accuracy of the state of the lesion Z can be further improved.

Furthermore, in the aspiration system 100 described above, the controller 21 of the aspiration device 2 acquires the length information and flow passage diameter information regarding the lesion Z from the X-ray image data and the ultrasound image data, but the present disclosure is not limited to this configuration. The aspiration system 100 may include a device including a controller that acquires the length information and flow passage diameter information regarding the lesion Z from the X-ray image data and the ultrasound image data separately from the aspiration device 2. Then, the aspiration device 2 may acquire the length information and flow passage diameter information regarding the lesion Z from this device.

Furthermore, the controller 21 of the aspiration device 2 described above acquires the length L itself of the lesion Z from the image data as the length information of the lesion Z of the blood vessel BV, but may acquire another information with which the length L of the lesion Z can be specified, such as position information with which the length L can be calculated.

Furthermore, the controller 21 of the aspiration device 2 described above acquires the flow passage occlusion rate as the flow passage diameter information of the lesion Z, but may acquire another information regarding the degree of occlusion of the flow passage, such as the minimum diameter of the flow passage of the lesion Z.

Figure 7A:
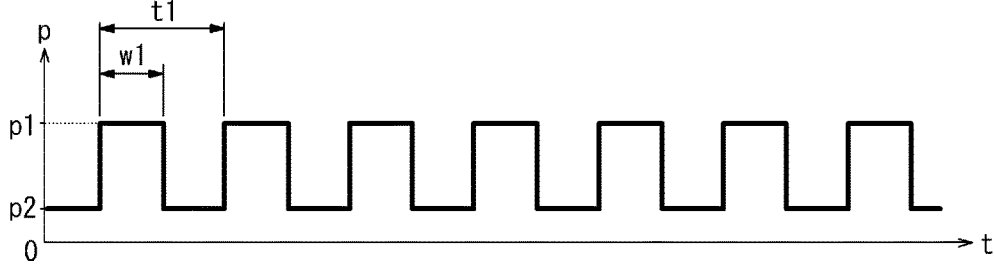
FIGS. 7A through 7D are diagrams each illustrating a modification example of aspiration control in a second aspiration mode of the aspiration device illustrated in FIGS. 6B to 6D.

Moreover, the controller 21 of the aspiration device 2 described above executes, as the second aspiration mode, control of repeating a state in which the aspiration pressure is zero and a state in which the aspiration pressures are predetermined aspiration pressure p1 and p0 in a pulse wave form (see FIGS. 6B to 6D), but the present disclosure is not limited to this control. As illustrated in FIG. 7A, the controller 21 may execute, as the second aspiration mode, control of repeating a state in which the aspiration pressure is a low aspiration pressure p2 and a state in which the aspiration pressure is an aspiration pressure p1 higher than the aspiration pressure p2 in a pulse wave form. That is, the negative pressure state is maintained, and there may be no time for the aspiration pressure to become zero. However, from the viewpoint of suppressing the rapid change in the blood flow rate before and after the removal of the foreign substance described above, it is preferable to provide a time when the aspiration pressure becomes zero, and conversely, a positive pressure state may be provided. In the case of the positive pressure, there is a possibility that thrombus moves to the peripheral side, and thus it is desirable to install a thrombus trap mechanism such as a net on the distal side with respect to the lesion Z in advance.

Figure 7B:
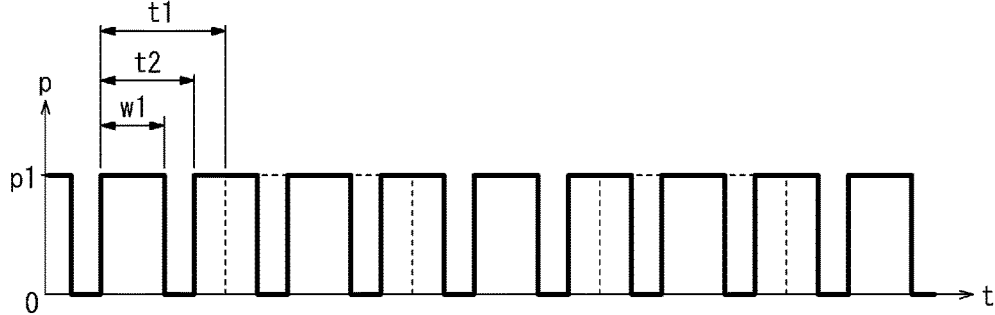

Furthermore, in the above-described example, the aspiration flow rate per minute is controlled by varying the aspiration pressure ("p" in FIGS. 6A to 6D) and the aspiration time in one aspiration period ("w" in FIGS. 6A to 6D), but the present disclosure is not limited to such control. As illustrated in FIG. 7B, the controller 21 of the aspiration device 2 may vary the aspiration flow rate per minute by varying the aspiration period in the second aspiration mode. Specifically, in FIG. 7B, a broken line indicates control for the aspiration pressure p1, aspiration time w1 in one aspiration period, and aspiration period t1 in the low flow rate mode. Furthermore, in FIG. 7B, a solid line indicates control for the aspiration pressure p1, aspiration time w1 in one aspiration period, and aspiration period t2 in the high flow rate mode. In this manner, the aspiration flow rate per minute may be varied by varying the aspiration period. It can be achieved by varying two or more of the aspiration pressure, aspiration time in one aspiration period, and aspiration period.

Figure 7C:
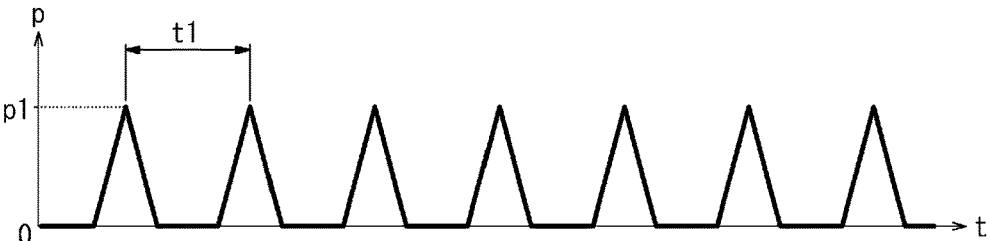
Figure 7D:
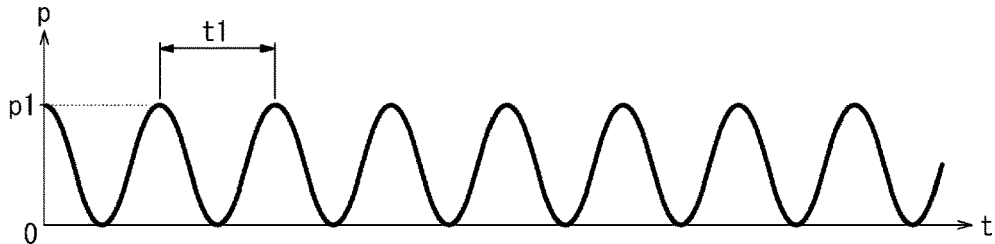

Moreover, as illustrated in FIGS. 6B to 6D, the controller 21 of the aspiration device 2 described above is configured to apply the aspiration pressure in a rectangular wave shape in the second aspiration mode, but is not limited to this configuration. As illustrated in FIGS. 7C and 7D, the controller 21 may be configured to apply the aspiration pressure in a triangular wave shape (see FIG. 7C) or a sinusoidal wave shape (see FIG. 7D).

Furthermore, in addition to the configuration of the above-described embodiment, the aspiration system 100 may have a mechanism for locally administering a thrombolytic agent to the foreign substance such as the thrombus Y at the lesion Z (see FIG. 1). Therefore, the efficiency of destructing the foreign substance such as the thrombus Y may be improved.

What is claimed is:

1. An aspiration device for aspirating an object in a blood vessel, comprising:

a pump connectable to an aspiration catheter and capable of applying a negative pressure to the aspiration catheter; and a controller configured to:

acquire a length of an abnormal part of the blood vessel in which the object exists and an occlusion rate of the abnormal part, select either a first aspiration mode in which the pressure applied to the aspiration catheter is maintained at a certain level or a second aspiration mode in which the pressure is varied, and control the pump to apply the pressure according to the selected aspiration mode, wherein the second aspiration mode includes a low flow rate mode and a high flow rate mode, an aspiration flow rate of the high flow rate mode being higher than that of the low flow rate mode, and the controller is further configured to select:

the high flow rate mode of the second aspiration mode when the length of the abnormal part of the blood vessel is greater than a first threshold and the occlusion rate is equal to or less than a second threshold, and the low flow rate mode of the second aspiration mode when the length of the abnormal part of the blood vessel is equal to or less than the first threshold and the occlusion rate is greater than the second threshold.

2. The aspiration device according to claim 1, wherein the controller selects the first aspiration mode when the length of the abnormal part of the blood vessel is equal to or less than the first threshold and the occlusion rate is equal to or less than the second threshold.

3. The aspiration device according to claim 2, wherein the controller selects the second aspiration mode either when the length of the abnormal part of the blood vessel is greater than the first threshold or when the occlusion rate is greater than the second threshold.

4. The aspiration device according to claim 3, wherein the controller is configured to control the pump to vary the pressure in the second aspiration mode based on the length of the abnormal part of the blood vessel and the occlusion rate.

5. The aspiration device according to claim 1, wherein the second aspiration mode includes another mode, an aspiration flow rate of which is higher than that of the high flow rate mode, and the controller selects said another mode when the length of the abnormal part of the blood vessel is greater than the first threshold and the occlusion rate is greater than the second threshold.

6. The aspiration device according to claim 1, wherein the controller is configured to determine a maximum value of the pressure applied to the aspiration catheter in the second aspiration mode based on at least one of a hardness of a normal part of the blood vessel in which the object does not exist and a hardness of the object.

7. The aspiration device according to claim 1, wherein the controller is configured to determine a maximum value of the pressure applied to the aspiration catheter in the second aspiration mode based on changes in the pressure.

8. The aspiration device according to claim 1, further comprising:

an interface circuit connectable to one or more imaging devices configured to acquire image data of the blood vessel, wherein the controller is configured to determine the length of the abnormal part of the blood vessel and the occlusion rate using the image data acquired by the imaging devices.

9. The aspiration device according to claim 1, wherein the controller is configured to set the aspiration flow rate of the high flow rate mode to be higher than that of the low flow rate mode by making an aspiration period in the high flow rate mode shorter than an aspiration period in the low flow rate mode.

10. The aspiration device according to claim 1, wherein the controller is configured to control the pump in the second aspiration mode to vary the pressure in a pulse wave form repeating a first negative pressure state and a second negative pressure state that is stronger than the first negative pressure state, such that the pressure is maintained at a negative value without becoming zero.

11. The aspiration device according to claim 1, wherein the controller is configured to control the pump in the second aspiration mode to vary the pressure in a triangular wave shape or a sinusoidal wave shape.

12. An aspiration system for aspirating an object in a blood vessel, comprising:

an aspiration catheter to be inserted into the blood vessel; and an aspiration device connectable to the aspiration catheter, capable of applying a negative pressure to the aspiration catheter, and configured to:

acquire a length of an abnormal part of the blood vessel in which the object exists and an occlusion rate of the abnormal part, select either a first aspiration mode in which the pressure applied to the aspiration catheter is maintained at a certain level or a second aspiration mode in which the pressure is varied, and apply the pressure to the aspiration catheter according to the selected aspiration mode, wherein the second aspiration mode includes a low flow rate mode and a high flow rate mode, an aspiration flow rate of the high flow rate mode being higher than that of the low flow rate mode, and the aspiration device is further configured to select:

the high flow rate mode of the second aspiration mode when the length of the abnormal part of the blood vessel is greater than a first threshold and the occlusion rate is equal to or less than a second threshold, and the low flow rate mode of the second aspiration mode when the length of the abnormal part of the blood vessel is equal to or less than the first threshold and the occlusion rate is greater than the second threshold.

13. The aspiration system according to claim 12, further comprising:

one or more imaging devices configured to acquire image data of the blood vessel, wherein the aspiration device is configured to determine the length of the abnormal part of the blood vessel and the occlusion rate using the image data acquired by the imaging devices.

14. The aspiration system according to claim 13, wherein the imaging devices include at least one of an X-ray imaging device configured to image the blood vessel from an outside of a living body and an ultrasound imaging device configured to image the blood vessel from an inside of the blood vessel using ultrasound.

15. An aspiration method for aspirating an object in a blood vessel, the method comprising:

acquiring a length of an abnormal part of a blood vessel in which the object exists and an occlusion rate of the abnormal part;

selecting either a first aspiration mode in which a negative pressure applied to an aspiration catheter is maintained at a certain level or a second aspiration mode in which the pressure is varied; and applying the pressure to the aspiration catheter inserted in the blood vessel according to the selected aspiration mode, wherein the second aspiration mode includes a low flow rate mode and a high flow rate mode, an aspiration flow rate of the high flow rate mode being higher than that of the low flow rate mode, and selecting includes selecting:

the high flow rate mode of the second aspiration mode when the length of the abnormal part of the blood vessel is greater than a first threshold and the occlusion rate is equal to or less than a second threshold, and the low flow rate mode of the second aspiration mode when the length of the abnormal part of the blood vessel is equal to or less than the first threshold and the occlusion rate is greater than the second threshold.

16. The aspiration method according to claim 15, wherein the first aspiration mode is selected when the length of the abnormal part of the blood vessel is equal to or less than the first threshold and the occlusion rate is equal to or less than the second threshold.

17. The aspiration method according to claim 16, wherein the second aspiration mode is selected when the length of the abnormal part of the blood vessel is greater than the first threshold or the occlusion rate is greater than the second threshold.

18. The aspiration method according to claim 17, further comprising:

varying the pressure applied to the aspiration catheter in the second aspiration mode based on the length of the abnormal part of the blood vessel and the occlusion rate.

* * * * *